(12) United States Patent
Gilmour et al.

(10) Patent No.: US 7,972,866 B2
(45) Date of Patent: Jul. 5, 2011

(54) BIOSENSOR AND ULTRASONIC METHOD OF MAKING A BIOSENSOR

(75) Inventors: Steven B. Gilmour, Coral Gables, FL (US); Keith A. Harvey, Oakland Park, FL (US)

(73) Assignee: Nipro Diagnostics, Inc., Ft. Lauderdale, FL (US)

( * ) Notice: Subject to any disclaimer, the term of this patent is extended or adjusted under 35 U.S.C. 154(b) by 992 days.

(21) Appl. No.: 11/764,471

(22) Filed: Jun. 18, 2007

(65) Prior Publication Data

US 2008/0311004 A1    Dec. 18, 2008

(51) Int. Cl.
G01N 21/75    (2006.01)
B29C 65/00    (2006.01)

(52) U.S. Cl. .................. 436/166; 422/425; 156/73.1
(58) Field of Classification Search .................. 436/166; 422/425; 156/73.1
See application file for complete search history.

(56) References Cited

U.S. PATENT DOCUMENTS

| | | | |
|---|---|---|---|
| 3,649,358 A | 3/1972 | Johnson, II | |
| 4,213,810 A | 7/1980 | Heynisch et al. | |
| 4,639,078 A | 1/1987 | Sheem | |
| 5,158,843 A | 10/1992 | Batson et al. | |
| 5,262,193 A | 11/1993 | Louks et al. | |
| 5,328,728 A | 7/1994 | Swirbel et al. | |
| 5,366,579 A | 11/1994 | Yamazaki et al. | |
| 5,451,260 A | 9/1995 | Versteeg et al. | |
| 5,571,410 A | 11/1996 | Swedberg et al. | |
| 5,846,359 A * | 12/1998 | Ota et al. | 156/73.1 |
| 5,932,302 A | 8/1999 | Yamazaki et al. | |
| 6,468,605 B2 | 10/2002 | Shah et al. | |
| 6,583,071 B1 | 6/2003 | Weidman et al. | |
| 6,676,988 B2 | 1/2004 | Chan et al. | |
| 6,706,337 B2 | 3/2004 | Hebert | |
| 6,743,635 B2 | 6/2004 | Neel et al. | |
| 6,835,523 B1 | 12/2004 | Yamazaki et al. | |
| 6,841,052 B2 | 1/2005 | Musho et al. | |
| 7,015,046 B2 | 3/2006 | Wohlstadter et al. | |
| 7,018,795 B2 | 3/2006 | Kinoshita et al. | |
| 7,041,068 B2 | 5/2006 | Freeman et al. | |

(Continued)

FOREIGN PATENT DOCUMENTS

EP    0 078 990 A1    5/1983

(Continued)

OTHER PUBLICATIONS

International Search Report and the Written Opinion of the International Searching Authority in International Application No. PCT/US2008/066069, mailed Sep. 30, 2008.

(Continued)

Primary Examiner — Lore Jarrett
(74) Attorney, Agent, or Firm — Finnegan, Henderson, Farabow, Garrett & Dunner, L.L.P.

(57) ABSTRACT

There is provided a test strip for testing a fluid sample, including a sample cavity configured to receive the fluid sample and an ultrasonically-spread reagent layer arranged on at least one surface of the sample cavity. There is also provided a method for making a biosensor, including providing a substrate having a region for receiving a sample; dispensing a liquid substance on at least one surface of the region for receiving a sample; and subjecting the substrate to ultrasonic vibrations to quickly and uniformly spread the liquid substance on the at least one surface of the region for receiving a sample.

27 Claims, 5 Drawing Sheets

U.S. PATENT DOCUMENTS

| | | |
|---|---|---|
| 7,045,054 B1 | 5/2006 | Buck et al. |
| 2001/0021411 A1 | 9/2001 | Shah et al. |
| 2003/0203498 A1* | 10/2003 | Neel et al. ................. 436/95 |
| 2007/0135698 A1 | 6/2007 | Shah et al. |

FOREIGN PATENT DOCUMENTS

| | | | |
|---|---|---|---|
| EP | 0 276 782 | A2 | 8/1988 |
| EP | 0 969 282 | A2 | 1/2000 |
| WO | WO 93/13408 | A | 7/1993 |
| WO | WO 03/091717 | A1 | 11/2003 |
| WO | WO 2007/033079 | A2 | 3/2007 |

OTHER PUBLICATIONS

Moroney, R.M. et al., "Ultrasonically Induced Microtransport," Published in Micro Electro Mechanical Systems, MEMS (1991).

* cited by examiner

BIOSENSOR AND ULTRASONIC METHOD OF MAKING A BIOSENSOR

BACKGROUND OF THE INVENTION

1. Field of the Invention

The present invention generally relates to biosensors and methods for making biosensors. The present invention also relates in particular to electrochemical biosensors for sensing blood glucose levels and methods for making electrochemical biosensors for sensing blood glucose levels.

2. Discussion of the Background Art

Many people can benefit from conveniently and reliably monitoring one or more physiological parameters. For example, diabetics must generally monitor their blood glucose level on a frequent basis and may do so using various diagnostic systems. These systems typically include a test strip and a meter configured to determine the blood glucose level in a blood sample introduced to the test strip. More generally, it can be very useful in many industrial settings to conveniently and reliably monitor various samples (e.g., food, water, oil, chemicals, etc.) for various types of constituents, whether to detect the presence of normally absent constituents, to ascertain the concentration of certain constituents, etc.

The aforementioned test strip and meter may determine the blood glucose level (or another relevant physiological parameter) in a blood sample using various technologies. Among these, electrochemical technologies are prevalent because they allow the relatively rapid and accurate determination of the blood glucose level using a very small blood sample, usually less than 1 μl.

An electrochemical test strip contains a biosensor typically formed in a sample cavity containing suitable reagents and electrodes. In the case of diabetics seeking to measure their blood glucose level, reagents suitable for glucose will, upon introducing a blood sample into the sample cavity, react with any glucose present in the blood sample. Thereafter, in amperometric systems, the meter will apply a voltage to the electrodes to cause a redox reaction, resulting in a current from which the blood glucose level may be determined. Such exemplary biosensor systems can be found in commonly-assigned U.S. Pat. No. 6,743,635, which is incorporated herein by reference in its entirety. Other methodologies, such as potentiometry and coulometry are also known in the art.

There is an ongoing need for test strips and meters that are accurate and reliable because a precise knowledge of blood glucose levels may be critical to the health of a diabetic. Moreover, evolving market demands are imposing new and increasingly stringent performance requirements, including the ability to measure blood glucose levels using smaller blood sample sizes and the ability to complete those measurements in a shorter time. These new requirements entail reductions in the dimensions of the test strip and its sample cavity and electrodes, and, in turn, create new manufacturing challenges.

Among these new manufacturing challenges are those involving the uniform introduction of a small sample to the biosensor. The biosensor's reagents can be disposed on any surface of the sample cavity, e.g., using micropipetting or aerosolization, or any other technique known in the art to deposit fluid onto a small surface. When the sample enters the sample cavity and comes into contact with the surface covered by the reagent, the reagent can react with the target analyte in the sample. When the volume of the reagent is relatively large, uniform spreading occurs relatively easily. However, when the volume of the reagent is small, the reagent will usually be disposed on the surface in small droplets that generally tend to either remain at the location where they were dispensed, without uniformly spreading, or, at best, spread very slowly. Surfactants may be added to the reagent to lower its liquid surface tension and thereby facilitate spreading to an extent, but the use of surfactants does not sufficiently accelerate spreading and often fails to promote spreading sufficiently to fully cover the surface of the sample cavity designed to be exposed to the sample.

In addition, the slow spreading of the reagent on the surface of the sample cavity can be a significant problem because it leads to manufacturing delays, since spreading must be complete prior to drying the reagent, and because such slow spreading causes non-uniformity of the reagent layer, which can negatively impact test accuracy and precision.

"Ultrasonic sprays," where a solution to be sprayed or deposited is atomized using an ultrasonic nozzle before being sprayed, have been used to create uniform depositions, See U.S. Pat. Nos. 5,451,260; 6,468,605; 6,583,071; and 6,706,337, which are all incorporated herein in their entirety. Ultrasonic vibrations have also been used in other contexts, such as ion bombardment or radioisotope coating. See U.S. Pat. Nos. 6,835,523; 5,932,302; and 6,676,988, which are all incorporated herein in their entirety. Finally, ultrasonic vibrations have also been used to coat a dipped optical fiber. See U.S. Pat. No. 4,639,078, which is incorporated herein in its entirety. However, none of these references pertains to the spreading of droplets or addresses the aforementioned biosensor manufacturing challenges.

SUMMARY OF THE INVENTION

Disclosed herein are various novel processes for manufacturing a biosensor including a reagent layer that is spread quickly and uniformly on the surface of a sample cavity, despite small dimensions of the biosensor.

More specifically, disclosed herein is a test strip for testing a blood sample, including: a base layer; a spacer layer arranged on the base layer; a cover layer arranged on the spacer layer; a sample cavity configured to receive the blood sample and defined by the base, spacer, and cover layers; and an ultrasonically-spread reagent layer arranged on at least one surface of the sample cavity.

Moreover, a novel method for making a biosensor is disclosed herein, including spreading a reagent layer quickly and uniformly on a surface of a sample cavity, notwithstanding the relatively small dimensions of the resulting biosensor.

In accordance with the above, there is further disclosed a method for making a biosensor, including the steps of: providing a substrate having a region for receiving a sample; dispensing a liquid substance on at least one surface of the region for receiving a sample; and subjecting the substrate to ultrasonic vibrations to quickly and uniformly spread the liquid substance on the at least one surface of the region for receiving a sample.

Further, there is provided a method for manufacturing a plurality of biosensors, including: arranging a plurality of test strips into an array; providing each test strip in the array with a sample cavity; dispensing a liquid solution on at least one surface of the sample cavity of each test strip in the array; and subjecting the sample cavity of each test strip in the array to ultrasonic vibrations to quickly and uniformly spread the liquid solution on the at least one surface of the sample cavity of each test strip in the array.

Still further, there is provided a method for making a plurality of test strips, including the steps of: arranging a plurality of test strips into an array, each test strip including (1) a base layer, (2) a spacer layer arranged on the base layer, (3) a cover layer arranged on the spacer layer, and (4) a sample cavity defined by the base, spacer, and cover layers; dispensing a liquid reagent layer on a surface of the sample cavity; and passing the array over an ultrasonic generator to subject the sample cavity of each test strip to ultrasonic vibrations to quickly and uniformly spread the liquid reagent layer.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention or limiting in any way.

BRIEF DESCRIPTION OF THE DRAWINGS

The accompanying drawings, which are incorporated in and constitute a part of this specification, illustrate exemplary embodiments of the invention and, together with the description, serve to explain the principles of the invention and are not restrictive of the invention or limiting in any way.

DESCRIPTION OF THE PREFERRED EXEMPLARY EMBODIMENTS

Figure 1:
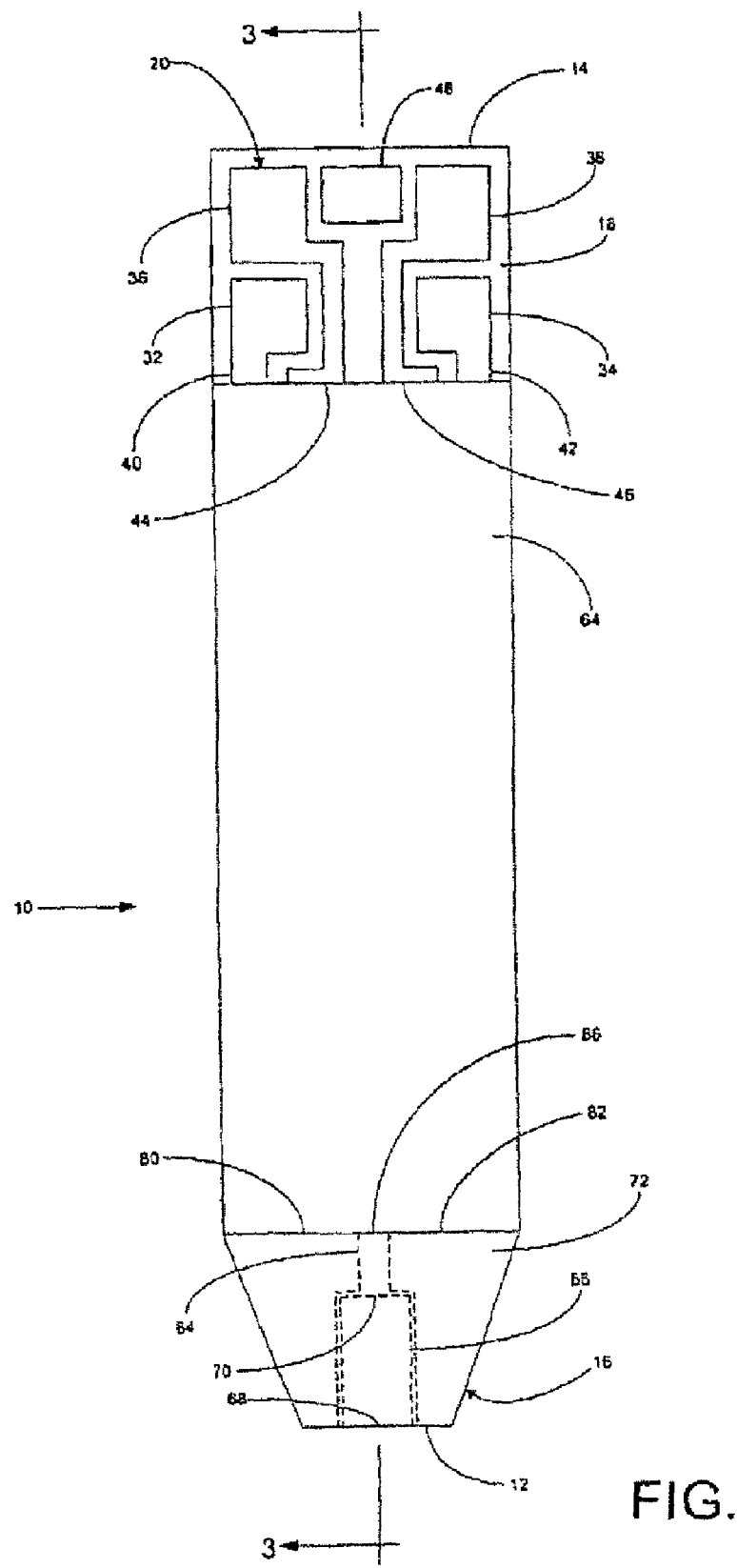
FIG. 1 is a top view of a test strip according to an illustrative embodiment of the present invention.
Figure 2:
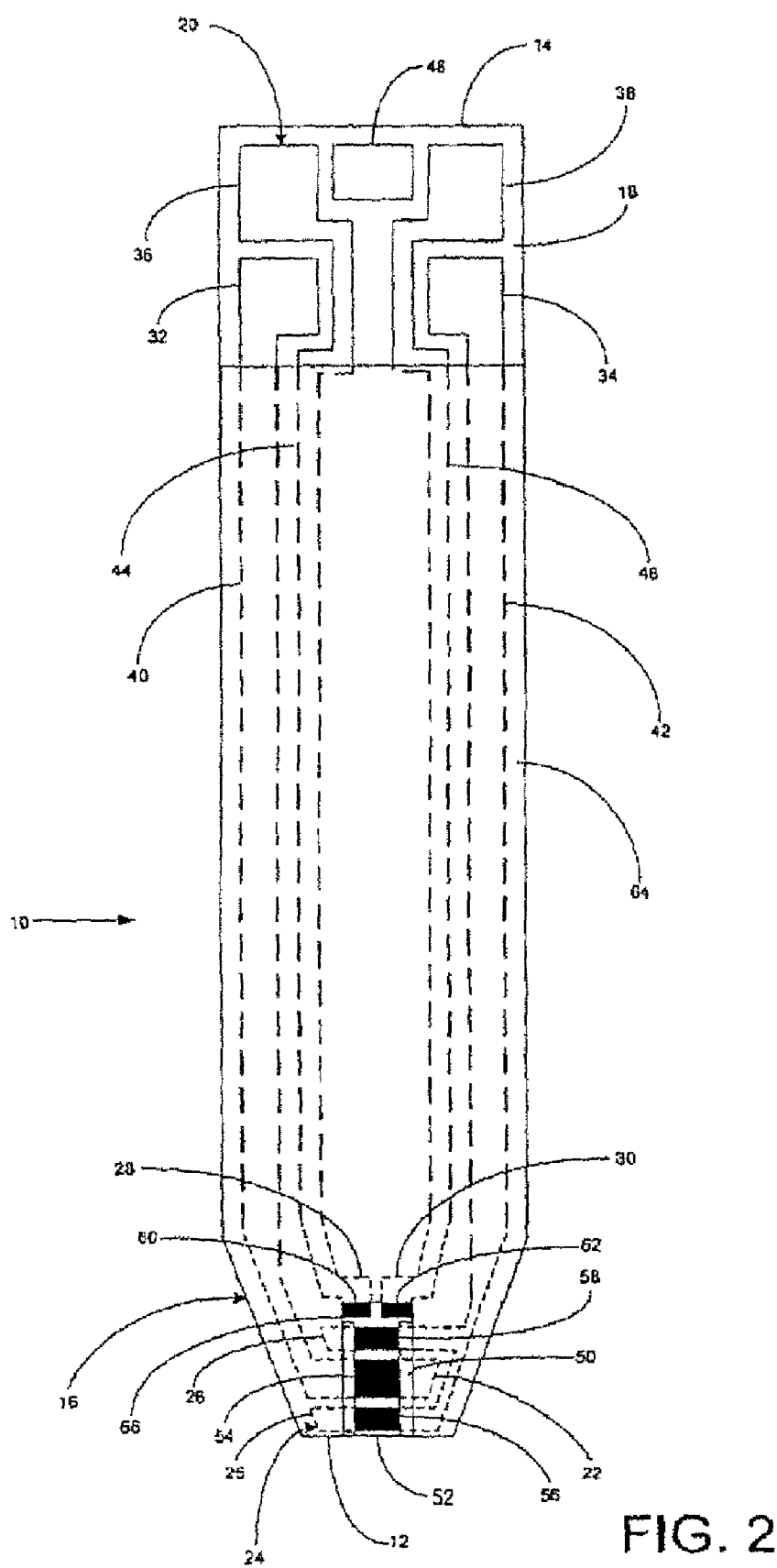
FIG. 2 is a top view of a test strip according to an illustrative embodiment of the present invention as in FIG. 1, except that certain elements were removed to reveal other elements not seen in FIG. 1.
Figure 3:
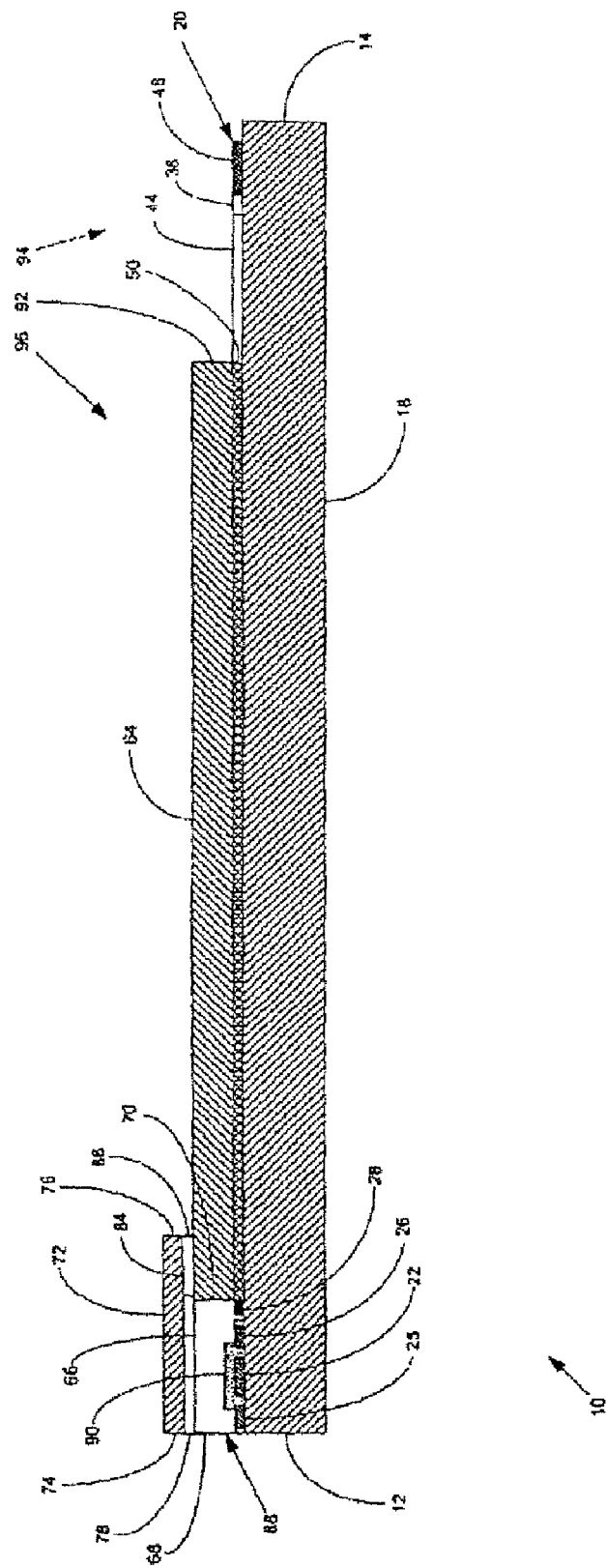
FIG. 3 is a cross-section of the test strip of FIG. 1 taken along line 3-3 according to an illustrative embodiment of the present invention.

FIGS. 1-3 illustrate a test strip 10 according to an illustrative embodiment of the present invention. Of course, any configuration of biosensor can be used. The test strip 10 extends from a proximal end 12 to a distal end 14 and includes an opening in the proximal end 12 to receive a blood sample. The test strip 10 may also include a tapered section 16, where the width of the distal end 14 tapers down to the width of the proximal end 12, to help the user to rapidly locate the opening where the blood sample is to be applied.

The illustrative test strip 10 can have a generally layered construction as shown in FIG. 3. A base layer 18, composed of an insulating material, may extend along the entire length of the test strip 10. A conductive pattern 20, which may be disposed on the base layer 18, includes a plurality of electrodes arranged near the proximal end 12, a plurality of electrical contacts arranged near the distal end 14, and a plurality of conductive traces connecting the electrodes to the electrical contacts. The conductive pattern 20 also can include an auto-on conductor 48 disposed on the base layer 18 near the distal end 14.

The plurality of electrodes can include, for example, a working electrode 22, a first section 25 of a counter electrode 24, a second section 26 of the counter electrode 24, a fill-detect anode 28, and a fill-detect cathode 30. The electrodes may include any material known in the art to be suitable for functioning as an electrode and may have been made using any manner or microfabrication techniques known in the art. The electrical contacts include a working electrode contact 32, a counter electrode contact 34, a fill-detect anode contact 36, and a fill-detect cathode contact 38. The conductive traces include a working electrode trace 40 connecting working electrode 22 to working electrode contact 32, a counter electrode trace 42 connecting counter electrode 24 to counter electrode contact 34, a fill-detect anode trace 44 connecting fill-detect anode 28 to fill-detect anode contact 36, and a fill-detect cathode trace 46 connecting fill-detect cathode 30 to fill-detect cathode contact 38.

A dielectric layer 50 including an insulating material may also be disposed on the base layer 18. The dielectric layer 50 does not cover the auto-on conductor 48 and the electrical contacts 32, 34, 36, and 38. The dielectric layer 50 covers most of the base layer 18 and all portions of the conductive pattern 20 extending from a line just proximal of contacts 32 and 34 to the proximal end 12, except for a slot 52, which extends from the proximal end 12 and defines an exposed portion 54 of working electrode 22, exposed portions 56 and 58 of sections 25 and 26 of counter electrode 24, an exposed portion 60 of fill-detect anode 28, and an exposed portion 62 of fill-detect cathode 30.

A dielectric spacer layer 64, disposed on the dielectric layer 50, may include a slot 66 that is substantially aligned with slot 52 and which extends from a proximal end 68 aligned with the proximal end 12 to a distal end 70, so that exposed portions 54, 56, 58, 60, and 62 of working electrode 22, counter electrode 24, fill-detect anode 28, and fill-detect cathode 30 are located in slot 66. The edge of the dielectric spacer layer 64 closest to the distal end 14 may define a shoulder 92, which may in turn define a thin section 94 of test strip 10 extending between the shoulder 92 and the distal end 14, and a thick section 96 extending between the shoulder 92 and proximal end 12. Numerous alternative configurations of the dielectric spacer layer are of course possible. In particular, the dielectric layer could be absent and the dielectric spacer layer 64 could itself define the electrodes.

A cover 72, which can be transparent, with a proximal end 74 and a distal end 76, may be attached using an adhesive layer 78 to the dielectric spacer layer 64. The adhesive layer 78 may include first and second sections 80 and 82 arranged on opposite sides of slot 66, and may be separated by a break 84 extending from the distal end 70 of slot 66 to an opening 86.

The test strip 10 includes a sample cavity 88 defined by the base layer 18, along with the slot 66 and the cover 72, for receiving a blood sample. The sample cavity 88 as illustrated has a first opening, defined by the proximal end 68 of slot 66, through which the blood sample is introduced into sample cavity 88. The sample cavity 88 also has a second opening, defined by the break 84 at the distal end 70 of slot 66, for venting the sample cavity 88. The openings could be modified in various ways and could have any suitable shape. Each of the first and second openings could be also be substituted by a plurality of openings, arranged in any configuration over any subset of the surfaces of the sample cavity and configured to perform the same function as a single opening. The sample cavity may also preferably be dimensioned to draw the blood sample in through the first opening by capillary action. Alternatively, the sample cavity may be dimensioned to draw the blood sample in through the first opening using any method known in the art to displace fluid.

An ultrasonically-spread reagent layer 90 is disposed in sample cavity 88. The ultrasonically-spread reagent layer 90 can cover at least the exposed portion 54 of working electrode 22, or, alternatively, the ultrasonically-spread reagent layer 90 is also at least partially in contact with the exposed portions 56 and 58 of counter electrode 24. Of course, the ultrasonically-spread reagent layer 90 could be spread over any area of the sample cavity 88 as long as at least part of that area is exposed to the sample. For example, that area could be the entirety of each of the surfaces of the sample cavity that are exposed to the sample, could be the entirety of one or more of the surfaces of the sample cavity that are exposed to the sample, or could be any patterned area arranged on one or more of the surfaces of the sample cavity that are exposed to the sample and derived using any microfabrication technique. Exemplary methods by which the ultrasonically-spread reagent layer 90 can be spread ultrasonically are further discussed below.

In the case of a glucose sensor, the ultrasonically-spread reagent layer 90 includes chemical constituents suitable to obtain an electrochemical measurement of the level of glucose in the blood sample. For example, the ultrasonically-spread reagent layer 90 may include an enzyme specific for glucose (e.g., glucose oxidase) and a mediator (e.g., ruthenium hexaamine or potassium ferricyanide). The ultrasonically-spread reagent layer 90 may also include one or more other components, such as buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485).

In the case of an exemplary glucose-sensing ultrasonically-spread reagent layer reagent layer 90, as discussed above, the glucose oxidase would react with glucose in the blood sample and trigger a reaction that would oxidize glucose to gluconic acid and reduce ferricyanide to ferrocyanide. An appropriate voltage applied to working electrode 22, relative to counter electrode 24, would then oxidize ferrocyanide to ferricyanide, thereby generating a current that is related to the glucose concentration in the blood sample. Uniform spreading is desirable because any non-uniformity in the reagent layer could negatively impact the accuracy and precision of the sensor.

Figure 4:
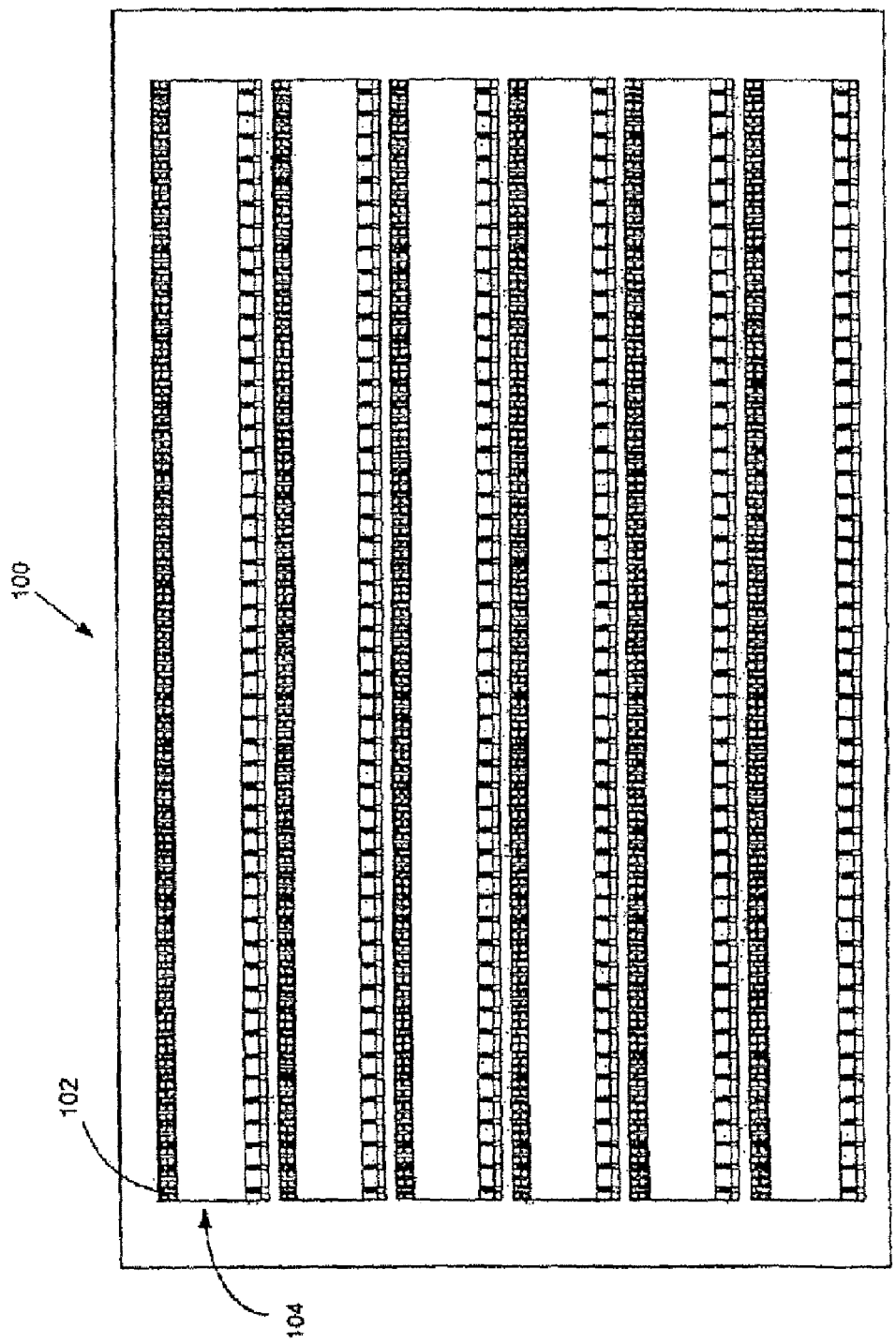
FIG. 4 is a schematic view of an array of test strips of the type shown in FIGS. 1-3 according to an illustrative embodiment of the present invention.

FIG. 4 illustrates a plurality of test strip structures 102 arranged in an integrated structure 100 suitable for mass production. The test strip structures 102 may be arranged in an array that includes a plurality of rows 104 each including a plurality of test strip structures 102. A plurality of test strips 10 may then be formed by separating the test strip structures 102 from each other. Preferably, each row 104 of test strip structures 102 is first punched out of integrated structure 100 during the separation process. A slitting process may subsequently be used to separate the test strip structures 102 in each row 104 into individual test strips 10.

Whether making one or a plurality of test strips, the ultrasonically-spread reagent layer 90 may be applied by first micropipetting or depositing a fluid composition onto the exposed portion 54 of working electrode 22. Alternatively, any other method which results in the application of reagent solution onto the exposed portion 54 can be used. The liquid composition is then subjected to ultrasonic vibrations to ensure that it is spread quickly and uniformly. In an exemplary method, the ultrasonically-spread reagent layer 90 can be allowed to dry. Preferably, the liquid composition has a pH of about 6 and contains about 2500 units of glucose oxidase per mL and 0.1 M potassium phosphate, along with polyvinyl alcohol, potassium phosphate, and hydroxyethylcellulose.

The present invention is in no way limited to the above exemplary structures, which could naturally be altered and modified in any way provided that at least one area of a cavity includes an ultrasonically-spread substance. Moreover, whereas the preferred embodiments discussed above are directed to a glucose biosensor useful in the field of medicine, they are merely used to conveniently illustrate the principles of the present invention. The use of an ultrasonically-spread substance in a cavity readily applies to the sensing, in any field or context, of any type of substance, whether currently known or to be discovered, provided that there is at least some element, molecule, or combination of one or more elements and/or molecules, in the ultrasonically-spread substance that can be used to obtain directly or indirectly any information regarding the substance to be sensed.

Generally, an exemplary test strip according to a preferred embodiment of the present invention may have a base layer, a spacer layer arranged on the base layer; a cover layer arranged on the spacer layer; a sample cavity configured to receive the blood sample and defined by the base, spacer, and cover layers; and an ultrasonically-spread reagent layer arranged on at least one surface of the sample cavity. The ultrasonically-spread reagent layer preferably includes at least an enzyme specific for glucose and an electron mediator. Alternatively, the ultrasonically-spread reagent layer may include any element or molecule, or any combination of elements and/or molecules, whether organic or inorganic, that would be known in the art to be able to yield information of any type about a substance of interest, which is not limited to glucose but could be anything that one would have a reason to sense.

The ultrasonically-spread reagent layer spread in the exemplary test strip can be spread using ultrasonic vibrations substantially perpendicular to the one or more surfaces of the sample cavity on which it was spread. The inertia of the reagent will resist such substantially perpendicular ultrasonic vibrations, and, as a result, the reagent is spread quickly and uniformly. In addition, the ultrasonically-spread reagent layer in the exemplary test strip is spread using ultrasonic vibrations at an angle to the one or more surfaces of the sample cavity in the range of about 60-90 degrees. If the reagent layer is spread on a plurality of surfaces of the sample cavity, some of which may be substantially non-parallel, the ultrasonically-spread reagent layer may be ultrasonically-spread in multiple steps to optimize spreading, e.g., by applying ultrasonic vibrations substantially in the range of about 60-90 degrees to each surface. Alternatively, the ultrasonically-spread reagent layer in the exemplary test strip may be spread using ultrasonic vibrations only on a selected one or more of the surfaces of the sample cavity.

The ultrasonically-spread reagent layer is spread in an exemplary embodiment using ultrasonic vibrations having a frequency between about 18 kHz and 50 kHz, or, more specifically, using ultrasonic vibrations having a frequency between about 20 kHz and 40 kHz. These ranges are provided as useful guidelines and are merely illustrative. Broader ranges, even beyond what is sometimes considered to be "ultrasonic" could also be used depending on the particular physical and/or chemical properties of the substance that is to be spread and of the surface on which it is to be spread. Along with suitable amplitudes, frequencies can be optimized to minimize any spreading into unwanted areas.

Figure 5:
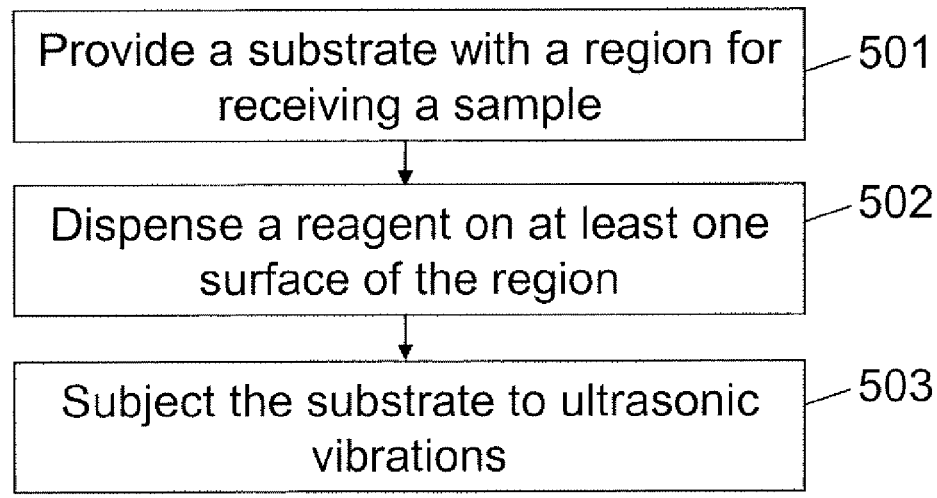
FIG. 5 is a diagram illustrating the steps of an exemplary method according to the present invention.

FIG. 5 illustrates steps in an exemplary method for making a biosensor according to an aspect of the present invention. The exemplary method includes step 501, which consists of providing a substrate having a region for receiving a sample; step 502, which consists of dispensing a liquid substance on at least one surface of the region for receiving a sample; and step 503, which consists of subjecting the substrate to ultrasonic vibrations to quickly and uniformly spread the liquid substance on the at least one surface of the region for receiving a sample. Naturally, other steps could be inserted before, after, or in between these steps as known in the art to make any other components of the biosensor or to refine upon these steps.

The exemplary method can include providing the substrate with a sample cavity having a volume between about 0.0001 mL and 1 mL. Of course, any size of cavity can be used. Alternatively, the providing step in the exemplary method can include providing the substrate with a sample cavity having a volume between about 0.0001 mL and 0.001 mL.

An exemplary method can also include dispensing at least one droplet of a reagent. The dispensing step may further include dispensing at least one droplet of a reagent including and enzyme specific for glucose and an electron mediator. Alternatively, or in addition, the dispensing step may further include dispensing at least one droplet of a reagent including any element or molecule, or any combination of elements and/or molecules, whether organic or inorganic, that would be known in the art to be able to yield information of any type about a substance of interest, which is not limited to glucose but could be anything that one would have a reason to sense. The dispensing step can also include the layering of different materials, each material being layered after the previous material has been layered and allowed to dry, and can further include mixing in situ.

In an illustrative method, ultrasonic vibrations can be generated using an ultrasonic horn. The ultrasonic horn can be in direct contact with the bottom of the substrate. The ultrasonic horn can also be located at a distance from 0.0001 mm to 10 cm from the sample cavity, or, alternatively, the ultrasonic horn can be located at a distance from 0.001 mm to 1 cm from the sample cavity. Alternatively, the subjecting step includes subjecting the substrate to ultrasonic vibrations using a method other than an ultrasonic horn such as using plasma-based or laser-based ultrasound generation methods.

Figure 6:
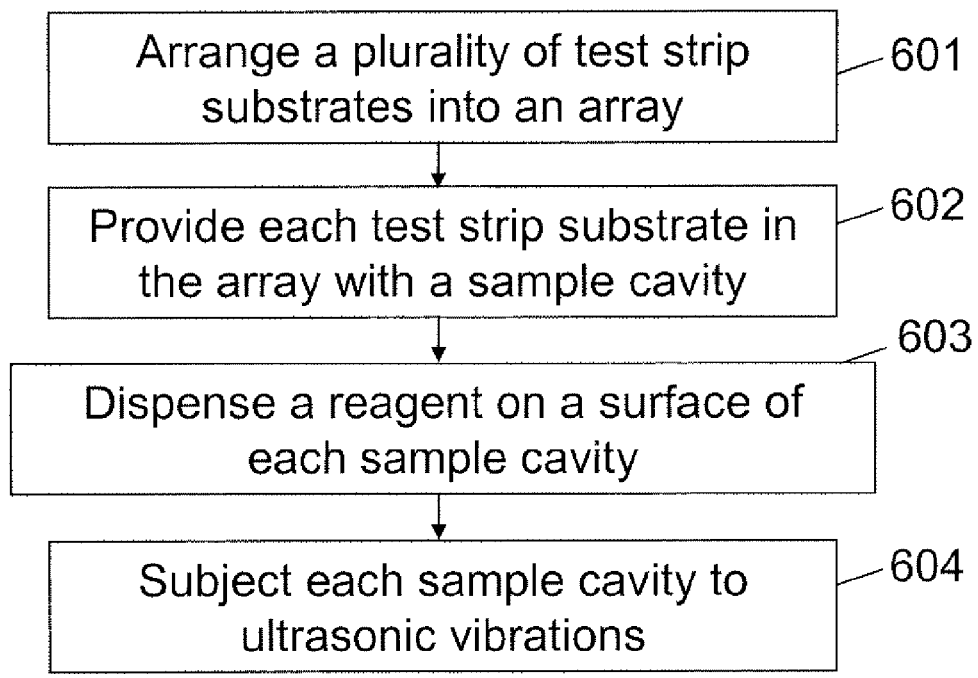
FIG. 6 is a diagram illustrating the steps of an exemplary method according to the present invention.

FIG. 6 illustrates steps in an exemplary method for making a plurality of biosensors according to an aspect of the present invention. The method includes step 601, which consists of arranging a plurality of test strip substrates into an array such as a sheet or a web, for example; step 602, which consists of providing each test strip substrate in the array with a sample cavity; step 603, which consists of dispensing a liquid solution on at least one surface of the sample cavity of each test strip in the array; and step 604, which consists of subjecting the sample cavity of each test strip in the array to ultrasonic vibrations to quickly and uniformly spread the liquid solution on the at least one surface of the sample cavity of each test strip in the array. Naturally, other steps could be inserted before, after, or in between these steps as known in the art to make any other components of the biosensor or to refine upon these steps.

Numerous other methods are possible and flow from this specification. Yet another exemplary method for making a plurality of test strips includes the steps of: arranging a plurality of test strips into an array, each test strip comprising (1) a base layer, (2) a spacer layer arranged on the base layer, and (3) a sample cavity defined by the base and spacer layers; dispensing a liquid reagent layer on a surface of the sample cavity; and passing the array over an ultrasonic generator to subject the sample cavity of each test strip to ultrasonic vibrations to quickly and uniformly spread the liquid reagent layer. Naturally, other steps could be inserted before, after, or in between these steps as know in the art to make any other component of the biosensor or to refine upon these steps.

The exemplary method can also include the step of passing the array over drying equipment to dry the ultrasonically-spread liquid reagent layer. The ultrasonically-spread liquid reagent layer can also be subjected to ultrasonic vibrations during drying, which has been found, unexpectedly, to contribute to a reduction in crystal size, a substantial benefit. The array can also be passed under or through the drying equipment. The drying equipment can be a convection oven. The drying equipment can also be based on infra-red heating. In one exemplary embodiments the array is passed under an infra-red heater.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for making a biosensor, comprising the steps of:
    providing a substrate having a region for receiving a sample;
    dispensing a liquid substance on a surface of the region for receiving a sample; and
    applying ultrasonic vibrations at an angle of about 60-90 degrees to the bottom of the substrate to quickly and uniformly spread the liquid substance on the surface of the region for receiving a sample.

2. The method of claim 1, wherein the providing step comprises providing the substrate with a sample cavity having a volume between about 0.0001 mL and 1 mL.

3. The method of claim 1, wherein the providing step comprises providing the substrate with a sample cavity having a volume between about 0.0001 mL and 0.001 mL.

4. The method of claim 1, wherein the dispensing step comprises dispensing at least one droplet of a reagent including an enzyme specific for glucose.

5. The method of claim 1, wherein the dispensing step comprises dispensing at least one droplet of a reagent including an electron mediator.

6. The method of claim 1, wherein the ultrasonic vibration are applied at a frequency between about 18 kHz and 50 kHz.

7. The method of claim 6, wherein the ultrasonic vibrations are applied at a frequency of about 20 kHz.

8. The method of claim 6, wherein the ultrasonic vibrations are applied at a frequency of about 40 kHz.

9. The method of claim 1, wherein the ultrasonic vibrations are applied using an ultrasonic horn.

10. A method for manufacturing a plurality of biosensors, comprising:
    arranging a plurality of test strip substrates into an array;
    providing each test strip substrate in the array with a sample cavity;
    dispensing a liquid solution on a surface of the sample cavity of each test strip in the array; and
    subjecting the sample cavity of each test strip in the array to ultrasonic vibrations to quickly and uniformly spread the liquid solution on the surface of the sample cavity of each test strip in the array, wherein the ultrasonic vibrations are applied at an angle of about 60-90 degrees to the bottom of the sample cavity of each test strip in the array.

11. The method of claim 10, wherein the providing step comprises providing each test strip in the array with a sample cavity having a volume between about 0.0001 mL and 1 mL.

12. The method of claim 10, wherein the providing step comprises providing each test strip in the array with a sample cavity having a volume between about 0.0001 mL and 0.001 mL.

13. The method of claim 10, wherein the dispensing step comprises dispensing a reagent on a bottom surface of the sample cavity of each test strip in the array, the reagent including an enzyme specific for glucose.

14. The method of claim 10, wherein the dispensing step comprises dispensing a reagent on a bottom surface of the sample cavity of each test strip in the array, the reagent including an electron mediator.

15. The method of claim 10, wherein the subjecting step comprises subjecting the sample cavity of each test strip in the array to ultrasonic vibrations having a frequency between about 18 kHz and 50 kHz.

16. The method of claim 15, wherein the subjecting step comprises subjecting the sample cavity of each test strip in the array to ultrasonic vibrations having a frequency of about 20 kHz.

17. The method of claim 15, wherein the subjecting step comprises subjecting the sample cavity of each test strip in the array to ultrasonic vibrations having a frequency of about 40 kHz.

18. The method of claim 10, wherein the subjecting step comprises subjecting the sample cavity of each test strip in the array to ultrasonic vibrations by passing the array of test strips over an ultrasonic horn.

19. A method for making a plurality of test strips, comprising the steps of:
   arranging a plurality of test strips into an array, each test strip comprising (1) a base layer, (2) a spacer layer arranged on the base layer, and (3) a sample cavity defined by the base and spacer layers;
   dispensing a liquid reagent layer on a surface of the sample cavity; and
   passing the array over an ultrasonic generator to subject the sample cavity of each test strip to ultrasonic vibrations to quickly and uniformly spread the liquid reagent layer, and wherein the passing step comprises subjecting the sample cavity of each test strip in the array to ultrasonic vibrations that are between about 60-90 degrees to the surface of the sample cavity.

20. The method of claim 19, comprising the step of passing the array over, under, or through drying equipment to dry the ultrasonically spread liquid reagent layer.

21. The method of claim 19, wherein the arranging step comprises:
   forming a plurality of electrodes on the base layer of each test strip, the plurality of electrodes comprising a working electrode, a counter electrode, and at least one fill-detect electrode; and
   forming a plurality of electrical contacts on the base layer of each test strip, the plurality of electrical contacts being electrically connected to the plurality of electrodes.

22. The method of claim 21, wherein the passing step comprises subjecting the sample cavity of each test strip in the array to ultrasonic vibrations having a frequency between about 18 kHz and 50 kHz.

23. The method of claim 22, wherein the passing step comprises subjecting the sample cavity of each test strip in the array to ultrasonic vibrations having a frequency between about 20 kHz and 40 kHz.

24. The method of claim 19, wherein the dispensing step comprises dispensing a liquid reagent layer including an enzyme specific for glucose and an electron mediator.

25. The method of claim 19, wherein the passing step comprises subjecting the sample cavity of each test strip in the array to ultrasonic vibrations having a frequency between about 18 kHz and 50 kHz.

26. The method of claim 25, wherein the passing step comprises subjecting the sample cavity of each test strip in the array to ultrasonic vibrations having a frequency of about 20 kHz.

27. The method of claim 25, wherein the passing step comprises subjecting the sample cavity of each test strip in the array to ultrasonic vibrations having a frequency of about 40 kHz.

* * * * *